US012251367B2

(12) United States Patent
Cuenoud et al.

(10) Patent No.: US 12,251,367 B2
(45) Date of Patent: *Mar. 18, 2025

(54) MEDIUM CHAIN TRIGLYCERIDE COMPOSITIONS

(71) Applicant: SOCIÉTÉ DES PRODUITS NESTLÉ S.A., Vevey (CH)

(72) Inventors: Bernard Cuenoud, Cully (CH); Mojgan Masoodi, Eclublens (CH)

(73) Assignee: SOCIÉTÉ DES PRODUITS NESTLÉ S.A., Vevey (CH)

(*) Notice: Subject to any disclaimer, the term of this patent is extended or adjusted under 35 U.S.C. 154(b) by 0 days.

This patent is subject to a terminal disclaimer.

(21) Appl. No.: 18/518,044

(22) Filed: Nov. 22, 2023

(65) Prior Publication Data
US 2024/0082199 A1 Mar. 14, 2024

Related U.S. Application Data

(60) Continuation of application No. 17/158,328, filed on Jan. 26, 2021, now Pat. No. 11,857,527, which is a division of application No. 15/780,492, filed as application No. PCT/EP2016/079521 on Dec. 2, 2016, now Pat. No. 11,000,496.

(30) Foreign Application Priority Data

Dec. 4, 2015 (EP) .................................. 15197934

(51) Int. Cl.
A61K 31/21 (2006.01)
A23K 20/158 (2016.01)
A23L 33/12 (2016.01)

(52) U.S. Cl.
CPC ............ A61K 31/21 (2013.01); A23K 20/158 (2016.05); A23L 33/12 (2016.08); A23V 2002/00 (2013.01)

(58) Field of Classification Search
CPC ...................................................... A61K 31/21
See application file for complete search history.

(56) References Cited

U.S. PATENT DOCUMENTS

| | | | |
|---|---|---|---|
| 9,447,016 B2 | 9/2016 | Boulos et al. | |
| 9,763,971 B2 | 9/2017 | Groenendijk et al. | |
| 10,548,866 B2 | 2/2020 | Williams et al. | |
| 11,000,496 B2 * | 5/2021 | Cuenoud | A61P 25/16 |
| 11,857,527 B2 * | 1/2024 | Cuenoud | A61P 25/16 |
| 2001/0006959 A1 | 7/2001 | Palzkill et al. | |
| 2002/0006959 A1 | 1/2002 | Henderson | |
| 2007/0179197 A1 | 8/2007 | Henderson | |
| 2015/0164840 A1 | 6/2015 | O'Donnell et al. | |
| 2016/0038552 A1 | 2/2016 | Bredesen et al. | |

FOREIGN PATENT DOCUMENTS

| | | |
|---|---|---|
| CN | 101405054 A | 4/2009 |
| EP | 2351491 A | 8/2011 |
| EP | 2484358 A1 | 8/2012 |
| JP | 2013543882 A | 12/2013 |
| JP | 2014534225 A | 12/2014 |
| JP | 5702292 B2 | 4/2015 |
| JP | 2015522256 A | 8/2015 |
| JP | 2016514673 A | 5/2016 |
| WO | 0182928 A1 | 11/2001 |
| WO | 2010052847 A1 | 5/2010 |
| WO | 20150052847 A | 5/2010 |
| WO | 2013186570 A1 | 12/2013 |

OTHER PUBLICATIONS

Rebello et al., "Pilot Feasibility and Safety Study Examining the Effect of Medium Chain Triglyceride Supplementation in Subjects with Mild Cognitive Impairment: A Randomized Controlled Trial", BBA Clinical, vol. 3, Jan. 16, 2015, pp. 123-125.
Odle et al., "Utilization of Medium-Chain Triglycerides by Neonatal Piglets: Chain Length of Even- and Odd-Carbon Fatty Acids and Apparent Digestion/Absorption and Hepatic Metabolism", The Journal of Nutrition, vol. 121, Issue No. 05, 1991, pp. 605-614.
European Office Action for Appl No. 16 809 686.5-1112 dated Apr. 28, 2023.
Galante et al., "Medium-Chain Triglycerides", Handbook of Functional Lipids, 2005, pp. 177-183.
Brazil Office Action for Appl No. BR112018009288-6 dated Jun. 5, 2023.
Veggiotti et al., Dietary Treatments and New Therapeutic Perspective in GLUT1 Deficiency Syndrome, Current Treatment Options in Neurology vol. 16, Article No. 291 (2014).
Hughes et al., The ketogenic diet component decanoic acid increases mitochondrial citrate synthase and complex I activity in neuronal cells, J Neurochem, May 2014;129(3):426-33.

(Continued)

Primary Examiner — Svetlana M Ivanova
(74) Attorney, Agent, or Firm — K&L Gates LLP

(57) ABSTRACT

A composition comprising medium-chain triglycerides (MCTs) wherein the composition comprises (i) a MCT comprising three fatty acid moieties each with 8 carbon atoms (MCT-C8) and (ii) a MCT comprising three fatty acid moieties each with 10 carbon atoms (MCT-C10); wherein the ratio of MCT-C8 to MCT-C10 is from 10:90 to 90:10 (mol/mol) and wherein the combined amount of MCT-C8 and MCT-C10 make up at least 50 mol % of the MCTs in the composition.

13 Claims, 3 Drawing Sheets

(56) References Cited

OTHER PUBLICATIONS

Sato, "Plasma ketone levels in neonatal calves fed medium chain triglycerides in milk", Journal of Veterinary Medical Science—Nihon Juigaku Zasshi, Japanese Society of Veterinary Science, Tokyo, Jp, vol. 56, No. 4, Aug. 1, 1994 (Aug. 1, 1994), pp. 781-782.
Tetrick et al., Blood D-(-)-3-hydroxybutyrate concentrations after oral administration of trioctanoin, trinonanoin, or tridecanoin to newborn rhesus monkeys (Macaca mulatta), Comp Med., Dec. 2010;60(6):486-90.
Henderson et al, "Study of the ketogenic agent AC-1202 in mild to moderate Alzheimer's disease: a randomized, double-blind, placebo-controlled, multicenter trial", Nutrition & Metabolism, Biomed Central. London, GB, vol. 6, No. 1, Aug. 10, 2009 (Aug. 10, 2009).
Japanese Office Action for Patent Appl. 2018-525699 dated Oct. 12, 2021.
Tetrick et al. "Blood D-(-)-3-Hydroxybutyrate Concentrations after Oral Administration of Trioctanoin, Trinonanoin, or Tridecanoin to Newborn Rhesus Monkeys (Macaca mulatta)" Comparative Medicine, Dec. 2010, vol. 60, No. 6, pp. 486-490.
Chang et al., "Seizure Control by Decanoic Acid through Direct AMPA Receptor Inhibition", Brain, vol. 139(Pt 2), 2016, pp. 431-443.
Hughes et al., The Ketogenic Diet Component Decanoic Acid increases Mitochondrial Citrate Synthase and Complex I Activity in Neuronal Cells, Journal of Neurochemistry, vol. 129, 2014, 426-433.
Malapaka et al., "Identification and Mechanism of 10-Carbon Fatty Acid as Modulating Ligand of Peroxisome Proliferator-Activated Receptors", Journal of Biological Chemistry, vol. 287, Issue No. 1, Jan. 2, 2012, pp. 183-195.
Wilde, "MCT Oil vs Brain Octane Oil", Retrieved from https://blog.livehelfi.com/en/mct-oil-vs-brain-octane-oil, Jun. 8, 2015, pp. 1-7.
Japan Patent Office Communication for Application No. P2018-525699, Dispatch No. 241166, Dispatch Date Jun. 23, 2020, 8 pages.
China Patent Office Communication for Application No. 201680067187.4, dated Jun. 3, 2020, 10 pages.
Nishi et al. (Changes in subcellular distribution of n-octanoyl or n-decanoyl ghrelin in ghrelin-producing cells. Front. Endocrinol., Jul. 9, 2013.
Gahete et al. (U Role of ghrelin system in neuroprotection and cognitive functions: Implications in Alzheimer's disease Peptides vol. 32, Issue 11, Nov. 2011, pp. 2225-2228.
Communication for Application No. 16809686.5 dated May 31, 2022.

\* cited by examiner

MEDIUM CHAIN TRIGLYCERIDE COMPOSITIONS

CROSS REFERENCE TO RELATED APPLICATIONS

This application is a continuation of U.S. application Ser. No. 17/158,328 filed Jan. 26, 2021, which is a divisional of U.S. application Ser. No. 15/780,492 filed May 31, 2018, which is a National Stage of International Application No. PCT/EP2016/079521 filed Dec. 2, 2016, which claims priority to European Patent Application No. 15197934.1 filed Dec. 4, 2015, the entire contents of which are incorporated herein by reference.

FIELD OF THE INVENTION

The present invention relates to a composition comprising medium chain triglycerides (MCTs), in particular MCT-C8 and MCT-C10. The present invention also relates to the use of the composition for providing ketones and/or C10 fatty acids to a subject. The present invention further relates to the use of the composition for the treatment or prevention of conditions associated with brain energy deficiency condition or disease and neurological conditions.

BACKGROUND TO THE INVENTION

Whilst glucose is understood to be the primary energy source of the mammalian brain, impaired glucose metabolism can produce an energy deficit in the brain, and may result in neuronal loss and morphological changes (Hoyer, 1990, Aging (Milano) 2:245-58).

Ketones such as acetone, acetoacetate and β-hydroxybutyrate can serve as an alternative energy source, particularly in periods of prolonged fasting or carbohydrate deficiency. Ketones can be readily used by mitochondria for ATP generation and can be used instead of glucose by neural tissue (Tetrick et al, 2010, Comparative Medicine 60:486-490). Ketones may also exert a protective effect on neurons from free radical damage (Vanitallie T B et al, 2003, Ketones: metabolism's ugly duckling. Nutr. Rev. 61:327-41).

Studies have suggested that ketone administration following ischaemic injury reduces the impact on the brain of the ischaemic injury. Indeed, ketone supplements have been considered as a therapeutic option in traumatic brain injury (White and Venkatesh, 2011, Critical Care 15:219). Furthermore, studies suggest that neurodegenerative diseases, such as Parkinson's disease and Alzheimer's disease, will benefit from ketone administration. By way of example, Reger et al, (2004, Neurobiol Aging. 25:311-4. 14) found that elevation of serum ketones levels in Alzheimer's patients raised the cognitive scores.

Free fatty acids may be metabolised to ketones and may also serve as an alternative source of energy because large quantities of ATP are released when fatty acids are metabolized.

Medium-chain triglycerides (MCTs) are medium-chain fatty acid esters of glycerol. After ingestion of MCTs, the esterified fatty acids are cleaved from the MCT by lipases, such as pancreatic and gastrointestinal lipases and the released medium chain fatty acids (MCFA) are transported as free fatty acids via the portal vein to the liver. MCTs can passively diffuse from the gastrointestinal tract to the portal system without requirement for modification like long-chain fatty acids or very-long-chain fatty acids (You et al, 2008, JPEN 32: 169-175).

MCTs offer a readily available noncarbohydrate fuel source because they are rapidly absorbed and metabolized into medium-chain fatty acids and ketones (Traul et al. Food Chem Toxicol 2000; 38: 79— 98). Ketones are actively transported to the brain by, for example, monocarboxylic transporter 1 (MCT1) where they are mainly metabolised by neurones. Free fatty acids, such as C8 free fatty acid and C10 free fatty acid, can also reach the brain by diffusion where they are mainly metabolised by astrocytes. Thus, medium-chain fatty acids may provide both a direct and an indirect brain fuel source.

Accordingly, free fatty acids and ketones produced from MCTs can provide an alternative energy source or a supplementary energy and may be used to treat a wide range of disorders including neurological disorders and conditions and disorders associated with brain energy deficiency.

SUMMARY OF THE INVENTION

The present inventor has surprisingly found that administering a blend comprising C8 and C10 MCTs wherein the MCTs are present as homotriglycerides (i.e. each MCT comprises either three C8 fatty acids attached to the glycerol backbone or three C10 fatty acids attached to the glycerol backbone) results in a greater proportion of ketones and free C10 fatty acids in a bodily fluid (such as plasma) than a corresponding composition wherein a proportion of the MCTs are present as heterotriglycerides (by heterotriglyceride it is meant that the MCT comprises a combination of C8 and C10 fatty acids attached to the glycerol backbone such as MCT(mixC8/10 2:1) or MCT(mixC8/10 1:2)).

In particular, the present inventor has surprisingly found that, at the same overall C8:C10 ratio, a blend comprising homotriglyceride MCTs comprising three fatty acid moieties each with 8 carbon atoms (referred to herein as MCT-C8) and (ii) homotriglyceride MCTs comprising three fatty acid moieties each with 10 carbon atoms (referred to herein as MCT-C10) results in a greater proportion of ketones and C10 free fatty acids in a bodily fluid (such as plasma) than a corresponding composition having a mixture of (i) MCT-C8, (ii) MCT-C10, (iii) MCT(mixC8/10 2:1) and (iv) MCT (mixC8/C10 1:2).

Accordingly, in a first aspect of the invention there is provided a composition comprising MCTs wherein the composition comprises a MCT-C8 and a MCT-C10, wherein the ratio of MCT-C8 to MCT-C10 is from 10:90 to 90:10 (mol/mol) and wherein the combined amount of MCT-C8 and MCT-C10 make up at least 50 mol % of the MCTs in the composition.

Preferably the combined amount of MCT-C8 and MCT-C10 make up at least 60, 70, 80, 90, 95, 98, or 99 mol % of the MCTs in the composition.

The ratio of MCT-C8 to MCT-C10 may be 20:80 to 85:15, 20:80 to 80:20, 30:70 to 85:15, 40:60 to 75:25, 50:50 to 70:30, 50:50 to 67:33, 55:45 to 65:35 or 58:42 to 62:38 (mol/mol).

In one embodiment the ratio of MCT-C8 to MCT-C10 is 58:42 to 62:38 (mol/mol).

In another embodiment the ratio of MCT-C8 to MCT-C10 is about 60:40 (mol/mol).

In one embodiment the ratio of MCT-C8 to MCT-C10 is 87:13 to 83:17 (mol/mol).

In another embodiment the ratio of MCT-C8 to MCT-C10 is about 85:15 (mol/mol).

In one embodiment the ratio of MCT-C8 to MCT-C10 is 18:82 to 22:78 (mol/mol).

In another embodiment the ratio of MCT-C8 to MCT-C10 is about 20:80 (mol/mol).

According to another aspect of the invention there is provided a composition comprising MCTs wherein the composition comprises a MCT-C8 and a MCT-C10, wherein the ratio of MCT-C8 to MCT-C10 is from 50:50 to 67:33 (mol/mol). The ratio of MCT-C8 to MCT-C10 may be 55:45 to 65:35 or 58:42 to 62:38 (mol/mol).

According to the present invention, MCT-C8 preferably comprises three octanoic acid moieties.

That is, the MCT-C8 preferably has the structure:

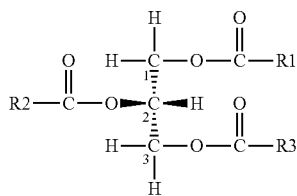

wherein R1, R2 and R3 are each $C_7H_{15}$.

According to the present invention, MCT-C10 preferably comprises three decanoic acid moieties.

That is, the MCT-C10 preferably has the structure:

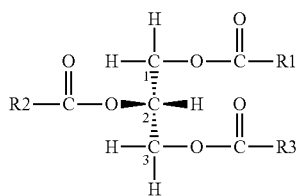

wherein R1, R2 and R3 are each $C_9H_{17}$.

In one embodiment at least 50, 60, 70, 80, 90, 95, 98, or 99 mol % of the MCTs in the composition are homotriglycerides.

Preferably the composition is free from or substantially free from any other MCT (i.e. aside from MCT-C8 and MCT-C10).

The composition may be free from or substantially free from any other triglycerides (i.e. aside from MCT-C8 and MCT-C10).

According to another aspect of the invention there is provided a composition of the invention for use in providing ketones (e.g., β-hydroxy butyrate (BHB) and/or aceto acetate (AcA)) and/or C10 fatty acids (e.g., decanoic acid) to a subject. The ketones and/or C10 fatty acids are preferably provided to the subject in a higher concentration than when using a corresponding composition wherein a greater proportion of the MCTs are present as heterotriglycerides.

According to another aspect of the invention there is provided a composition of the invention for use in the treatment or prevention of a brain energy deficiency condition or disease, a neurological condition, migraine, memory disorder, age-related memory disorder, brain injury, stroke, amyloid lateral sclerosis, multiple sclerosis, cognitive impairment, cognitive impairment post-intensive care, age-induced cognition impairment, Alzheimer's disease, Parkinson's disease, Huntingdon's disease, inherited metabolic disorders (such as glucose transporter type 1 deficiency syndrome and pyruvate dehydrogenase complex deficiency), bipolar disorder, schizophrenia, and/or epilepsy.

According to another aspect of the invention there is provided a composition of the invention for use in providing ketones and/or C10 fatty acids to a subject wherein the subject is suffering from a brain energy deficiency condition or disease, a neurological condition, migraine, memory disorder, age-related memory disorder, brain injury, stroke, amyloid lateral sclerosis, multiple sclerosis, cognitive impairment, cognitive impairment post-intensive care, age-induced cognition impairment, Alzheimer's disease, Parkinson's disease, Huntingdon's disease, inherited metabolic disorders (such as glucose transporter type 1 deficiency syndrome and pyruvate dehydrogenase complex deficiency), bipolar disorder, schizophrenia, and/or epilepsy.

In one embodiment exposure of the subject to ketones and/or C10 fatty acids following oral administration of the composition of the invention is greater than the exposure following oral administration of a composition comprising the MCT species shown below:

|  | Mole % |
|---|---|
| MCT-C8 | 22% |
| MCT-C10 | 10% |
| MCT(mix C8/C10) 2:1 | 34% |
| MCT(mix C8/C10) 1:2 | 34% |

Preferably the exposure of the subject to ketones and/or C10 fatty acids following oral administration of the composition of the invention is at least 2, 3, 4, 5, 6, 7, 8, 9 or 10 mol % greater than following oral administration of a composition comprising the MCT species shown in the above table.

Preferably the composition is administered enterally.

In one embodiment the composition may be in the form of a food stuff or a feed.

In an embodiment the composition may be in the form of a medical food, a tube feed, a nutritional supplement or a nutritional composition.

In another embodiment the composition may be in the form of a complete nutritional product. In another embodiment the composition may provide partial nutrition.

In another embodiment the composition is in the form of a powder, preferably a spray dried powder.

In one embodiment the composition is in the form of an oil-in-water emulsion.

In another embodiment the composition is in the form of a beverage, mayonnaise, salad dressing, margarine, low fat spread, dairy product, cheese spread, processed cheese, dairy dessert, flavoured milk, cream, fermented milk product, cheese, butter, condensed milk product, ice cream mix, soya product, pasteurised liquid egg, bakery product, confectionary product, confectionary bar, chocolate bar, high fat bar, liquid emulsion, spray-dried powder, freeze-dried powder, UHT pudding, pasteurised pudding, gel, jelly, yoghurt, or a food with a fat-based or water-containing filling.

The present invention also provides a method for providing ketones and/or C10 fatty acids to a subject wherein said method comprises administering to the subject a composition of the present invention.

According to another aspect of the present invention there is provided a method of treating or preventing a brain energy deficiency condition or disease, a neurological condition, migraine, memory disorder, age-related memory disorder, brain injury, stroke, amyloid lateral sclerosis, multiple sclerosis, cognitive impairment, cognitive impairment post-intensive care, age-induced cognition impairment, Alzheimer's disease, Parkinson's disease, Huntingdon's disease, inherited metabolic disorders (such as glucose transporter type 1 deficiency syndrome and pyruvate dehydrogenase complex deficiency), bipolar disorder, schizophrenia, and/or epilepsy in a subject wherein said method comprising administering to the subject a composition of the present invention.

According to another aspect of the present invention there is provided the use of a composition of the present invention for the manufacture of a medicament for providing ketones and/or C10 fatty acids to a subject.

According to another aspect of the present invention there is provided the use of a composition of the present invention for the manufacture of a medicament for the treatment or prevention of a brain energy deficiency condition or disease, a neurological condition, migraine, memory disorder, age-related memory disorder, brain injury, stroke, amyloid lateral sclerosis, multiple sclerosis, cognitive impairment, cognitive impairment post-intensive care, age-induced cognition impairment, Alzheimer's disease, Parkinson's disease, Huntingdon's disease, inherited metabolic disorders (such as glucose transporter type 1 deficiency syndrome and pyruvate dehydrogenase complex deficiency), bipolar disorder, schizophrenia, and/or epilepsy.

According to another aspect of the present invention there is provided the use of a composition of the present invention for providing ketones and/or C10 fatty acids to a subject.

DETAILED DESCRIPTION OF THE INVENTION

Medium-Chain Triglyceride (MCT)

Figure 1:
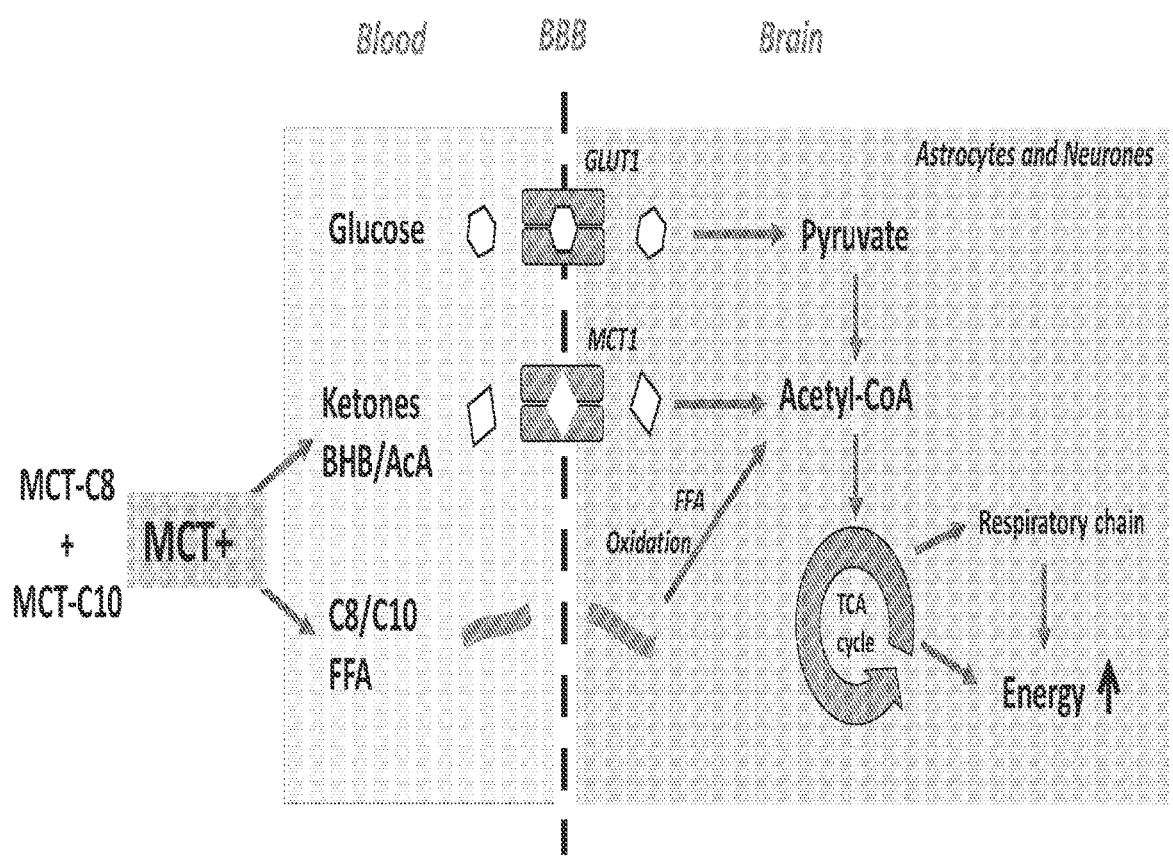
FIG. 1—schematic representation of glucose, ketones and free fatty acids (FFA) crossing the blood-brain barrier (BBB). The ketones (β-hydroxy butyrate—BHB) aceto acetate—AcA) and the free fatty acids (C8 FFA and C10 FFA) in this example are derived from MCT plus (MCT+). This Figure shows that MCT can act as a source of energy for the brain.

A triglyceride (also known as a triacylglycerol or a triacylglyceride) is an ester that is derived from glycerol and three fatty acids.

Fatty acids may be either unsaturated or saturated. Fatty acids which are not attached to other molecules are referred to as free fatty acids (FFA).

A medium-chain triglyceride (MCT) is a triglyceride in which all three fatty acid moieties are medium-chain fatty acid moieties. As defined herein, medium-chain fatty acids (MCFA) are fatty acids that have 6 to 12 carbon atoms. Medium-chain fatty acids with 8 carbon atoms may be referred to herein as C8 fatty acids or C8. Medium-chain fatty acids with 10 carbon atoms may be referred to herein as C10 fatty acids or C10.

The term "fatty acid moiety" refers to the part of the MCT that originates from a fatty acid in an esterification reaction with glycerol. In one example, an esterification reaction between glycerol and only octanoic acid would result in a MCT with octanoic acid moieties. In another example, an esterification reaction between glycerol and only decanoic acid would result in a MCT with decanoic acid moieties.

Octanoic acid (also known as caprylic acid) is a saturated fatty acid of the formula $CH_3(CH_2)_6COOH$.

Decanoic acid (also known as capric acid) is a saturated fatty acid of the formula $CH_3(CH_2)_8COOH$.

The composition of the present invention preferably comprises homotriglycerides (i.e.

all of the fatty acid moieties of the MCT are of the same identity, for example a C8 homotriglyceride may comprise 3 octanoic acid moieties).

The MCT may be a homotriglyceride comprising three fatty acid moieties each with 8 carbon atoms; this is referred to herein as MCT-C8. Preferably, all three fatty acid moieties of the MCT-C8 used in the composition of the present invention are octanoic acid moieties.

The MCT may be a homotriglyceride comprising three fatty acid moieties each with 10 carbon atoms; this is referred herein as MCT-C10. Preferably, all three fatty acid moieties of the MCT-C10 used in the composition of the present invention are decanoic acid moieties.

An MCT comprising one fatty acid moiety with 8 carbon atoms and wherein the remaining two fatty acid moieties have 10 carbon atoms is referred to herein as MCT(mixC8/10 1:2).

An MCT comprising two fatty acid moieties with 8 carbon atoms and wherein the remaining fatty acid moiety has 10 carbon atoms is referred to herein as MCT (mixC8/10 2:1).

Examples of natural sources of MCT include plant sources such as coconuts, coconut oil, palm kernels, palm kernel oils, and animal sources such as milk. Decanoic acid and octanoic acid form about 5-8% and 4-10% of the fatty acid composition of coconut oil, respectively.

MCTs may also be synthesised by esterification of glycerol with one or more medium-chain fatty acids (MCFA) with a tail of 6 to 12 carbon atoms. For example, MCT-C8 can be synthesised by esterification of glycerol with C8 fatty acids (e.g. octanoic acid) and MCT-C10 can be synthesised by esterification of glycerol with C10 fatty acids (e.g. decanoic acid).

Composition

There is provided herein a composition comprising medium-chain triglycerides (MCTs) wherein the composition comprises (i) a homotriglyceride MCT comprising three fatty acid moieties each with 8 carbon atoms (MCT-C8) and (ii) a homotriglyceride MCT comprising three fatty acid moieties each with 10 carbon atoms (MCT-C10).

In one embodiment, the ratio of MCT-C8 to MCT-C10 is from 10:90 to 90:10 (mol/mol).

In one embodiment, the ratio of MCT-C8 to MCT-C10 is from 20:80 to 85:15 (mol/mol). In another embodiment, the ratio of MCT-C8 to MCT-C10 is from 20:80 to 80:20 (mol/mol). In another embodiment, the ratio of MCT-C8 to MCT-C10 is from 30:70 to 85:15 (mol/mol). In one embodiment, the ratio of MCT-C8 to MCT-C10 is from 30:70 to 70:30 (mol/mol). In another embodiment the ratio of MCT- C8 to MCT-C10 is about 50:50 to about 70:30 (mol/mol). In another embodiment the ratio of MCT-C8 to MCT-C10 is about 50:50 to about 67:33 (mol/mol). In another embodiment the ratio of MCT-C8 to MCT-C10 is about 55:45 to about 65:35 (mol/mol). In another embodiment the ratio of MCT-C8 to MCT-C10 is about 56:44 to about 62:38 (mol/mol). In one embodiment the ratio of MCT-C8 to MCT-C10 is about 58:42 to about 62:38 (mol/mol).

In one embodiment the ratio of MCT-C8 to MCT-C10 is about 60:40 (mol/mol).

For example, the ratio of MCT-C8 to MCT-C10 may be about 90:10, about 89:11, about 88:12, about 87:13, about 86:14, about 85:15, about 84:16, about 83:17, about 82:18, about 81:19, about 80:20, about 79:21, about 78:22, about 77:23, about 76:24, about 75:25, about 74:26, about 73:27, about 72:28, about 71:29, 70:30, about 69:31, about 68:32, about 67:33, about 66:34, about 65:35, about 64:36, about 63:37, about 62:38, about 61:39, about 60:40, about 59:41, about 58:42, about 57:43, about 56:44, about 55:45, about 54:46, about 53:47, about 52:48, about 51:49, about 50:50, about 49:51, about 48:52, about 47:53, about 46:54, about 45:55, about 44:56, about 43:57, about 42:58, about 41:59, about 40:60, about 39:61, about 38:62, about 37:63, about 36:64, about 35:65, about 34:66, about 33:67, about 32:68, about 31:69, about 30:70, about 29:71, about 28:72, about 27:73, about 26:74, about 25:75, about 24:76, about 23:77, about 22:78, about 21:79, about 20:80, about 19:81, about 18:82, about 17:83, about 16:84, about 15:85, about 14:86, about 13:87, about 12:88, about 11:89 or about 10:90 (mol/mol).

Preferably at least 50, 60, 70, 80, 90, 95, 98, or 99 mol % of the MCTs in the composition are homotriglycerides.

Preferably at least 60, 70, 80, 90, 95%, 98, or 99 mol % of the MCTs in the composition are MCT-C8 and MCT-C10.

In one embodiment at least 60, 70, 80, 90, 95%, 98, or 99 mol % of the triglycerides in the composition are MCT-C8 and MCT-C10.

In one embodiment the composition according to the present invention is free from or substantially free from any other MCT. As used herein, the term "free from any other MCT" means that the composition does not comprise any MCT other than MCT-C8 and MCT-C10. As used herein, the term "substantially free from any other MCT" means that the composition comprises MCT-C8 and MCT-C10 but there may be traces (e.g., less than 3, 2, 1 or 0.5 mol %) of other MCTs.

In one embodiment the composition according to the present invention is free from or substantially free from any other triglycerides. As used herein, the term "free from any other triglycerides" means that the composition does not comprise any triglycerides other than MCT-C8 and MCT-C10. As used herein, the term "substantially free from any other triglycerides" means that the composition comprises MCT-C8 and MCT-C10 but there may be traces (e.g., less than 5, 3, 2, 1 or 0.5 mol %) of other triglycerides.

The composition may further comprise substances such as minerals, vitamins, salts, functional additives including, for example, palatants, colorants, emulsifiers, antimicrobial or other preservatives. Minerals that may be useful in such compositions include, for example, calcium, phosphorous, potassium, sodium, iron, chloride, boron, copper, zinc, magnesium, manganese, iodine, selenium, chromium, molybdenum, fluoride and the like. Examples of vitamins that may be useful in compositions described herein include water soluble vitamins (such as thiamin (vitamin B1), riboflavin (vitamin B2), niacin (vitamin B3), pantothenic acid (vitamin B5), pyridoxine (vitamin B6), biotin (vitamin B7), myo-inositol (vitamin B8) folic acid (vitamin B9), cobalamin (vitamin B12), and vitamin C) and fat soluble vitamins (such as vitamin A, vitamin D, vitamin E, and vitamin K) including salts, esters or derivatives thereof. Inulin, taurine, carnitine, amino acids, enzymes, coenzymes, and the like may be useful to include in various embodiments.

The composition may further comprise one or more agents that promote or sustain general neurologic health or further enhance cognitive function. Examples of such agents include choline, phosphatidylserine, alpha-lipoic acid, CoQ10, acetyl-L-carintine, herbal extracts (such as *Gingko biloba, Bacopa monniera, Convolvulus pluricaulis* and *Leucojum aestivum*), omega-3 or omega-6 polyunsaturated fatty acids (such as eicosapentaenoic acid, docosapentaenoic acid or docosahexaenoic acid as free fatty acid), aliphatic ester (such as ethylester, triglycerides or monoglycerides formats), and fish oil extracts.

In one embodiment the composition is in the form of a tablet, dragee, capsule, gel cap, powder, granule, solution, emulsion, suspension, coated particle, spray-dried particle or pill.

In another embodiment the composition may be in the form of a powder. The powder may, for example, be a spray-dried powder or a freeze-dried powder.

The composition may be usable for reconstitution in water.

The composition may be in the form of an emulsion. The emulsion may, for example, be an oil-in-water emulsion.

The composition may be inserted or mixed into a food substance. The composition may be in the form of a food stuff or a feed. In one embodiment the food stuff is a human food stuff.

The composition may be in the form of a medical food. The term "medical food" as used herein refers to a food product specifically formulated for the dietary management of a medical disease or condition; for example, the medical disease or condition may have distinctive nutritional needs that cannot be met by normal diet alone. The medical food may be administered under medical supervision. The medical food may be for oral ingestion or tube feeding.

The composition may be in the form of a tube feed. The term "tube feed" refers to a product which is intended for introducing nutrients directly into the gastrointestinal tract of a subject by a feeding tube. A tube feed may be administered by, for example, a feeding tube placed through the nose of a subject (such as nasogastric, nasoduodenal, and nasojejunal tubes), or a feeding tube placed directly into the abdomen of a subject (such as gastrostomy, gastrojejunostomy, or jejunostomy feeding tube).

The composition may be in the form of a nutritional composition or a nutritional supplement. The term "nutritional supplement" refers to a product which is intended to supplement the general diet of a subject.

The composition may be in the form of a complete nutritional product. The term "complete nutritional product" refers to a product which is capable of being the sole source of nourishment for the subject.

In various embodiments the composition may be in the form of a beverage, mayonnaise, salad dressing, margarine, low fat spread, dairy product, cheese spread, processed cheese, dairy dessert, flavoured milk, cream, fermented milk product, cheese, butter, condensed milk product, ice cream mix, soya product, pasteurised liquid egg, bakery product, confectionary product, confectionary bar, chocolate bar, high fat bar, liquid emulsion, spray-dried powder, freeze-dried powder, UHT pudding, pasteurised pudding, gel, jelly, yoghurt, or a food with a fat-based or water-containing filling.

In one embodiment the composition may be an infant formula.

In yet other embodiments the composition of the invention may be used to coat a food, snack, pet food, or pet treat.

The composition may in the form of a pharmaceutical composition and may comprise one or more suitable pharmaceutically acceptable carriers, diluents and/or excipients.

Examples of such suitable excipients for compositions described herein may be found in the "Handbook of Pharmaceutical Excipients, 2nd Edition, (1994), Edited by A Wade and P J Weller.

Acceptable carriers or diluents for therapeutic use are well known in the pharmaceutical art, and are described, for example, in Remington's Pharmaceutical Sciences, Mack Publishing Co. (A. R. Gennaro edit. 1985).

Examples of suitable carriers include lactose, starch, glucose, methyl cellulose, magnesium stearate, mannitol, sorbitol and the like. Examples of suitable diluents include ethanol, glycerol and water.

The choice of pharmaceutical carrier, excipient or diluent can be selected with regard to the intended route of administration and standard pharmaceutical practice. The pharmaceutical compositions may comprise as, or in addition to, the carrier, excipient or diluent any suitable binder(s), lubricant(s), suspending agent(s), coating agent(s), solubilising agent(s).

Examples of suitable binders include starch, gelatin, natural sugars such as glucose, anhydrous lactose, free-flow lactose, beta-lactose, corn sweeteners, natural and synthetic gums, such as acacia, tragacanth or sodium alginate, carboxymethyl cellulose and polyethylene glycol.

Examples of suitable lubricants include sodium oleate, sodium stearate, magnesium stearate, sodium benzoate, sodium acetate, sodium chloride and the like.

Preservatives, stabilizers, dyes and even flavouring agents may be provided in the composition. Examples of preservatives include sodium benzoate, sorbic acid and esters of p-hydroxybenzoic acid. Antioxidants and suspending agents may be also used.

Nutritionally acceptable carriers, diluents and excipients include those suitable for human or animal consumption and that are used as standard in the food industry. Typical nutritionally acceptable carriers, diluents and excipients will be familiar to the skilled person in the art.

Administration

The compositions as described herein may be administered enterally or parenterally.

Preferably, the composition is administered enterally. For example, the composition may be administered in the form of a food stuff or a supplement.

Enteral administration may be oral, gastric, and/or rectal.

In one embodiment, the composition is administered orally.

In general terms, administration of the composition as described herein may, for example, be by an oral route or another route into the gastro-intestinal tract, for example the administration may be by tube feeding.

The subject may be a mammal such as a human, canine, feline, equine, caprine, bovine, ovine, porcine, cervine and primates. Preferably the subject is a human.

In one embodiment the subject is an infant. The infant may, for example, be a human such as a newborn infant (i.e. a baby under 28 days of age) or a premature infant (i.e. a baby born before 37 completed weeks of gestation).

In one embodiment the subject is an aging subject. For instance, a subject may be an aging subject when it has reached 40, 50, 60, 66, 70, 75, or 80% of its likely lifespan.

A determination of lifespan may be based on actuarial tables, calculations, or estimates, and may consider past, present, and future influences or factors that are known to positively or negatively affect lifespan. Consideration of species, gender, size, genetic factors, environmental factors and stressors, present and past health status, past and present nutritional status, and stressors may be taken into consideration when determining lifespan. The aging subject may, for example, be a human subject over the age of 40, 45, 50, 55, 60, 65, 70, 75, 80, 85, 90, 95 or 100 years old.

Treatment

It is to be appreciated that all references herein to treatment include curative, palliative and prophylactic treatment. Treatment may also include arresting progression in the severity of a disease.

Both human and veterinary treatments are within the scope of the invention.

Free fatty acids and ketones produced from MCTs can provide an alternative energy source to glucose to supplement or replace the energy in cells such as astrocytes, myocytes, cardiomyocytes, or neuronal cells.

Brain tissue consumes a large amount of energy in proportion to its volume. In an average healthy subject, the brain gets most of its energy from oxygen-dependent metabolism of glucose. Typically, the majority of the brain's energy is used to help neurons or nerve cells send signals and the remaining energy is used for cell-health maintenance.

A deficiency in brain energy, for example caused by impairment of glucose utilisation, can result in neuronal hyperactivity, seizures and cognitive impairments.

Examples of brain energy deficiency conditions or diseases include: migraine, memory disorder, age-related memory disorder, brain injury, neurorehabilitation, stroke and post-stroke, amyloid lateral sclerosis, multiple sclerosis, cognitive impairment, cognitive impairment post-intensive care, age-induced cognition impairment, Alzheimer's disease, Parkinson's disease, Huntingdon's disease, inherited metabolic disorders (such as glucose transporter type 1 deficiency syndrome and pyruvate dehydrogenase complex deficiency), bipolar disorder, schizophrenia, and/or epilepsy.

As used herein the term "neurological condition" refers to a disorder of the nervous system. Neurological conditions may result from damage to the brain, spinal column or nerves, caused by illness or injury. Examples of the symptoms of a neurological condition include paralysis, muscle weakness, poor coordination, loss of sensation, seizures, confusion, pain and altered levels of consciousness. An assessment of the response to touch, pressure, vibration, limb position, heat, cold, and pain as well as reflexes can be carried out to determine whether the nervous system is impaired in a subject.

Some neurological conditions are life-long and the onset can be experienced at any time. Other neurological conditions, such as cerebral palsy, are present from birth. Some neurological conditions, such as Duchenne muscular dystrophy, commonly appear in early childhood, other neurological conditions, such as Alzheimer's disease and Parkinson's disease, affect mainly older people. Some neurological conditions have a sudden onset due to injury or illness, such as a head injury or stroke, or cancers of the brain and spine.

In one embodiment, the neurological condition is the result of traumatic damage to the brain.

In addition, or alternatively, the neurological condition is the result of an energy deficiency in the brain or in the muscles.

Examples of neurological conditions include migraine, memory disorder, age-related memory disorder, brain injury, neurorehabilitation, stroke and post-stroke, amyloid lateral sclerosis, multiple sclerosis, cognitive impairment, cognitive impairment post-intensive care, age-induced cognition impairment, Alzheimer's disease, Parkinson's disease, Huntingdon's disease, inherited metabolic disorders (such as glucose transporter type 1 deficiency syndrome and pyruvate dehydrogenase complex deficiency), bipolar disorder, schizophrenia, and/or epilepsy.

A migraine is an intense headache accompanied by other symptoms such as nausea (feeling sick), visual problems and an increased sensitivity to light or sound. A migraine may be preceded by an aura; the main symptoms of an aura are visual problems such as blurred vision (difficulty focussing), blind spots, flashes of light, or a zigzag pattern moving from the central field of vision towards the edge.

Strokes (also known as cerebrovascular accident (CVA) and cerebrovascular insult (CVI)) occur when there is poor blood flow to the brain resulting in cell death. There are two main types of stroke: ischemic, due to lack of blood flow, and haemorrhagic due to bleeding. Strokes result in part of the brain not functioning properly. The signs and symptoms of a stroke may include an inability to move or feel on one side of the body, problems understanding or speaking, feeling like the world is spinning, or loss of vision to one side. The signs and symptoms often appear soon after the stroke has occurred.

Amyotrophic lateral sclerosis (ALS) (also known as Lou Gehrig's disease, Charcot disease and motor neurone disease), involves the death of neurons responsible for controlling voluntary muscles. ALS is characterized by stiff muscles, muscle twitching, and gradually worsening weakness due to muscle wasting; this results in difficulty speaking, swallowing, and eventually breathing.

Multiple sclerosis affects the nerves in the brain and spinal cord, causing a wide range of symptoms including problems with muscle movement, problems with mobility and balance, numbness and tingling, blurring of vision (typically there is loss of vision in one eye) and fatigue.

Parkinson's disease is a degenerative disorder of the central nervous system mainly affecting the motor system. In the early course of the disease, the most obvious symptoms are movement-related; these include tremor at rest, rigidity, slowness of movement and difficulty with walking and gait. Later on in the course of the disease thinking and behavioural problems may arise, with dementia commonly occurring in the advanced stages of the disease. Other symptoms include depression, sensory, sleep and emotional problems.

Alzheimer's disease is a progressive neurodegenerative disorder. Alzheimer's disease is the most common cause of dementia. Symptoms include memory loss and difficulties with thinking, problem-solving or language. The mini mental state examination (MMSE) is an example of one of the tests used to diagnose Alzheimer's disease.

Huntington's disease is an inherited condition that damages certain nerve cells in the brain. Huntington's disease affects muscle coordination and leads to mental decline and behavioural symptoms. The earliest symptoms are often subtle problems with mood or cognition. A general lack of coordination and an unsteady gait often follow. As the disease advances, uncoordinated, jerky body movements become more apparent, along with a decline in mental abilities and behavioural symptoms. Physical abilities gradually worsen until coordinated movement becomes difficult. Mental abilities generally decline into dementia.

Inherited metabolic disorders are a range of diseases caused by defective genes. Typically the defective gene(s) results in a defect in an enzyme or in a transport protein which results in a block in the way that a compound is processed by the body such that there is a toxic accumulation of the compound. Inherited metabolic disorders can affect any organ and usually affect more than one. Symptoms often tend to be non-specific and usually relate to major organ dysfunction or failure. The onset and severity of a metabolic disorder may be exacerbated by environmental factors, such as diet and concurrent illness.

Glucose transporter type 1 (Glut1) deficiency syndrome is a genetic metabolic disorder involving the GLUT1 protein which transports glucose across the blood-brain barrier or the boundary separating tiny blood vessels from brain tissue. The most common symptom is seizures (epilepsy), which usually begin within the first few months of life. Additional symptoms that can occur include varying degrees of cognitive impairment and movement disorders characterized by ataxia, dystonia, and chorea. Glut1 deficiency syndrome may be caused by mutations in the SLC2A1 gene which produce GLUT1 protein.

Pyruvate dehydrogenase complex deficiency (pyruvate dehydrogenase deficiency or PDCD) is a neurodegenerative disorder associated with abnormal mitochondrial metabolism and disrupted carbohydrate metabolism. PDCD is characterized by the buildup of lactic acid in the body and a variety of neurological problems. Signs and symptoms of this condition usually first appear shortly after birth, and they can vary widely among affected individuals. The most common feature is a potentially life-threatening buildup of lactic acid (lactic acidosis), which can cause nausea, vomiting, severe breathing problems, and an abnormal heartbeat. Other symptoms include: neurological problems; delayed development of mental abilities and motor skills such as sitting and walking; intellectual disability; seizures; weak muscle tone (hypotonia); poor coordination, and difficulty walking. Some affected individuals have abnormal brain structures, such as underdevelopment of the tissue connecting the left and right halves of the brain (corpus callosum), wasting away (atrophy) of the exterior part of the brain known as the cerebral cortex, or patches of damaged tissue (lesions) on some parts of the brain. PDCD is a deficiency of one of the proteins in the pyruvate dehydrogenase complex (PDC). The pyruvate dehydrogenase complex comprises three enzymes identified as E1, E2, and E3; the E1 enzyme contains subunits identified as alpha and beta. The most common form of PDCD is caused by an abnormal gene in the E1 alpha subunit (the PDHA1 gene) located on the X chromosome. Some PDCD cases are caused by a mutation in a gene in another subunit of the pyruvate dehydrogenase complex such as the PDHX gene, the PDHB gene, the DLAT gene, the PDP1 gene, and the DLD gene.

Bipolar disorder is a brain disorder that causes unusual shifts in mood, energy, activity levels, and the ability to carry out day-to-day tasks. Bipolar disorder is characterized by periods of elevated mood and periods of depression. Bipolar disorder can be diagnosed using the guidelines from the *Diagnostic and Statistical Manual of Mental Disorders* (*DSM*) or the World Health Organization's International Statistical Classification of Diseases and Related Health Problems.

Schizophrenia is a chronic, severe, and disabling brain disorder in which individuals interpret reality abnormally. Schizophrenia may result in some combination of hallucinations, hearing voices, delusions, and extremely disordered thinking and behavior. Schizophrenia can be diagnosed using the guidelines from the *Diagnostic and Statistical Manual of Mental Disorders* (*DSM*) or the World Health Organization's International Statistical Classification of Diseases and Related Health Problems.

Epilepsy is a neurological disorder in which nerve cell activity in the brain becomes disrupted, causing seizures or periods of unusual behaviour, sensations and sometimes loss of consciousness.

The terms "cognitive impairment" and "cognition impairment" refer to disorders that give rise to impaired cognition, in particular disorders that primarily affect learning, memory, perception, and/or problem solving.

Cognitive impairment may occur in a subject after intensive care. Cognitive impairment may occur as part of the ageing process.

The term "cognition" refers to the set of all mental abilities and processes, including knowledge, attention, memory and working memory, judgment and evaluation, reasoning and "computation", problem solving and decision making, comprehension and production of language.

Levels of and improvements in cognition can be readily assessed by the skilled person using any suitable neurological and cognitive tests that are known in the art, including cognitive tests designed to assess speed of information processing, executive function and memory. Suitable example tests include Mini Mental State Examination (MMSE), Cambridge Neuropsychological Test Automated Battery (CANTAB), Alzheimer's Disease Assessment Scale-cognitive test (ADAScog), Wisconsin Card Sorting Test, Verbal and Figural Fluency Test and Trail Making Test, Wechsler Memory scale (WMS), immediate and delayed Visual Reproduction Test (Trahan et al. Neuropsychology, 1988 19(3) p. 173-89), the Rey Auditory Verbal Learning Test (RAVLT) (Ivnik, R J. et al. Psychological Assessment: A Journal of Consulting and Clinical Psychology, 1990 (2): p. 304-312), electroencephalography (EEG), magnetoencephalography (MEG), Positron Emission Tomography (PET), Single Photon Emission Computed Tomography (SPECT), Magnetic Resonance Imaging (MRI), functional Magnetic Resonance Imaging (fMRI), computerised tomography and long-term potentiation.

EEG, a measure of electrical activity of the brain, is accomplished by placing electrodes on the scalp at various landmarks and recording greatly amplified brain signals. MEG is similar to EEG in that it measures the magnetic fields that are linked to electrical fields. MEG is used to measure spontaneous brain activity, including synchronous waves in the nervous system.

PET provides a measure of oxygen utilisation and glucose metabolism. In this technique, a radioactive positron-emitting tracer is administered, and tracer uptake by the brain is correlated with brain activity. These tracers emit gamma rays which are detected by sensors surrounding the head, resulting in a 3D map of brain activation. As soon as the tracer is taken up by the brain, the detected radioactivity occurs as a function of regional cerebral blood flow. During activation, an increase in cerebral blood flow and neuronal glucose metabolism can be detected within seconds.

Suitable analysis can also be based on neuropsychiatric testing, clinical examinations and individual complaints of loss of cognitive function (e.g. subjective memory loss).

Further suitable tests may be based on assessments of locomotion, memory and attention, seizure susceptibility, and social interaction and/or recognition.

Memory disorders are the result of neurological damage to the brain structures such that the storage, retention and recollection of memories is hindered. Memory disorders can be progressive with age (e.g. Alzheimer's disease), or they can be immediate resulting, for example, from a head injury. Levels of and improvements in memory disorders can be readily assessed by the skilled person using any suitable tests that are known in the art such as Alzheimer's Disease Assessment Scale-cognitive test (ADAScog), Mini Mental State Examination (MMSE), computerised tomography (CT) scan, Magnetic Resonance Imaging (MRI), Single Photon Emission Computed Tomography (SPECT), Positron Emission Tomography (PET), and electroencephalography (EEG).

As used herein, the term "treatment" means to administer a composition as described herein to a subject having a condition in order to lessen, reduce or improve at least one symptom associated with the condition and/or to slow down, reduce or block the progression of the condition.

To "prevent" means to administer a composition as described herein to a subject is not showing any symptoms of the condition to reduce or prevent development of at least one symptom associated with the condition.

Ketones

After oral absorption, MCT are metabolised to free fatty acids and further metabolised to ketones. The free fatty acids are initially metabolised to β-hydroxy butyrate (BHB) and then aceto acetate (AcA).

MCFA and ketones can be produced in various amounts in bodily fluids depending on the MCT utilized, and they may be used as an alternative source of energy to glucose or to supplement the energy derived from glucose.

Ketones can be transported to the brain by, for example, monocarboxylic transporter 1 (MCT1) where they are mainly metabolised by neurones. Free fatty acids, such as C8 free fatty acids and C10 free fatty acids, can reach the brain by diffusion where they are mainly metabolised by astrocytes (see FIG. 1).

In one embodiment, the composition according to the present invention is for use in providing ketones and/or C10 fatty acids to a bodily fluid of a subject.

Preferably, the ketones are β-hydroxy butyrate and/or aceto acetate.

In one embodiment the exposure of the subject to ketones and/or C10 fatty acids following oral administration of the composition of the present invention is greater than following oral administration of a composition comprising the MCT species shown in Table 1:

TABLE 1

| Species in MCT(mixC8/C10 60:40) | Mole % |
|---|---|
| MCT-C8 | 22% |
| MCT-C10 | 10% |
| MCT(mix C8/C10) 2:1 | 34% |
| MCT(mix C8/C10) 1:2 | 34% |

In one embodiment the exposure of the subject to ketones and/or C10 fatty acids following oral administration of the composition according to the present invention is at least 1, 2, 3, 4, 5, 6, 7 or 8 mol % greater than following oral administration of a composition comprising the MCT species shown in Table 1.

In one embodiment the exposure of the subject to ketones and/or C10 fatty acids is quantified by measuring the levels of ketones and/or C10 fatty acids in the subject's plasma.

In one embodiment the exposure of the subject to ketones and/or C10 fatty acids is measured over 8 hours following oral administration.

The exposure of a subject to a ketone and/or C10 fatty acid may be calculated by determining the area under the curve (AUC) in a plot of concentration of ketone and/or C10 fatty acid in a bodily fluid e.g., blood plasma, against time (e.g. over 8 or 24 hours). Prior to analysis, biological fluids are either treated with organic solvent to precipitate protein and reconstituted in a mass spectrometry (MS) compatible solvent. Levels of ketone bodies and medium chain fatty acids are assessed using liquid chromatography coupled to high resolution mass spectrometry (LC-MS). In particular, β-hydroxy butyrate (BHB), aceto acetate (AcA), C8 fatty acids and C10 fatty acid concentrations are quantitatively measured using an external calibration methodology.

Various preferred features and embodiments of the present invention will now be described by way of non-limiting examples.

EXAMPLES

The practice of the present invention will employ, unless otherwise indicated, conventional techniques of chemistry, molecular biology, microbiology, recombinant DNA and immunology, which are within the capabilities of a person of ordinary skill in the art. Such techniques are explained in the literature. See, for example, J. Sambrook, E. F. Fritsch, and T. Maniatis, 1989, *Molecular Cloning: A Laboratory Manual,* Second Edition, Books 1-3, Cold Spring Harbor Laboratory Press; Ausubel, F. M. et al. (1995 and periodic supplements; *Current Protocols in Molecular Biology,* ch. 9, 13, and 16, John Wiley & Sons, New York, N.Y.); B. Roe, J. Crabtree, and A. Kahn, 1996, *DNA Isolation and Sequencing: Essential Techniques,* John Wiley & Sons; J. M. Polak and James O'D. McGee, 1990, *In Situ Hybridization: Principles and Practice;* Oxford University Press; M. J. Gait (Editor), 1984, *Oligonucleotide Synthesis: A Practical Approach,* Irl Press; D. M. J. Lilley and J. E. Dahlberg, 1992, *Methods of Enzymology: DNA Structure Part A: Synthesis and Physical Analysis of DNA* Methods in Enzymology, Academic Press; and E. M. Shevach and W. Strober, 1992 and periodic supplements, *Current Protocols in Immunology,* John Wiley & Sons, New York, NY. Each of these general texts is herein incorporated by reference.

Example 1—A Blend of MCT-C8 and MCT-C10 Provides More C10 FFA and Ketones than a MCT(C8/C10 MIX)

Materials and Methods

MCT Structures:

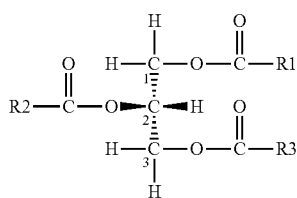

Ketone Structures:

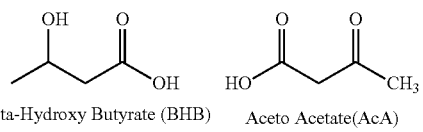

Beta-Hydroxy Butyrate (BHB)   Aceto Acetate (AcA)

TABLE 2

| MCT-C8 | | | MCT-C10 | | | MCT(C8/10 MIX) | | |
|---|---|---|---|---|---|---|---|---|
| R1 | R2 | R3 | R1 | R2 | R3 | R1 | R2 | R3 |
| $C_7H_{15}$ | $C_7H_{15}$ | $C_7H_{15}$ | | | | $C_7H_{15}$ | $C_7H_{15}$ | $C_7H_{15}$ |
| | | | | | | $C_7H_{15}$ | $C_7H_{15}$ | $C_9H_{17}$ |
| | | | | | | $C_7H_{15}$ | $C_9H_{17}$ | $C_7H_{15}$ |
| | | | | | | $C_9H_{17}$ | $C_7H_{15}$ | $C_7H_{15}$ |
| | | | | | | $C_7H_{15}$ | $C_9H_{17}$ | $C_9H_{17}$ |
| | | | | | | $C_9H_{17}$ | $C_7H_{15}$ | $C_9H_{17}$ |
| | | | | | | $C_9H_{17}$ | $C_9H_{17}$ | $C_7H_{15}$ |
| | | | $C_9H_{17}$ | $C_9H_{17}$ | $C_9H_{17}$ | $C_9H_{17}$ | $C_9H_{17}$ | $C_9H_{17}$ |
| One molecular species | | | One molecular species | | | 8 molecular species | | |

The MCT oil "PLUS" as used herein comprises (i) a homotriglyceride medium-chain triglyceride (MCT) comprising three fatty acid moieties each with 8 carbon atoms (MCT-C8) and (ii) a homotriglyceride MCT comprising three fatty acid moieties each with 10 carbon atoms (MCT-C10); wherein the ratio of MCT-C8 to MCT-C10 is about 60:40 (mol/mol).

Typically MCT oils are mixtures of triglycerides and homotriglycerides. The right-hand column of Table 2 details one such mixture. These oils were synthesised by esterification of glycerol with a mixture of C8 and C10 acid with a given ratio.

Mass Spectrum analysis of one MCT-mix (C8/C10 60:40) (the oil used to prepare Peptamen®) revealed that pure MCT-C8 (homotriglyceride) and MCT-C10 (homotriglyceride) amount to 32% only, the remaining 68% included a mixed backbone with C8:C10 ratio of 2:1 or 1:2, as shown below:

| Species in MCT(mixC8/C10 60:40) | Mole % |
|---|---|
| MCT-C8 | 22% |
| MCT-C10 | 10% |
| MCT(mix C8/C10) 2:1 | 34% |
| MCT(mix C8/C10) 1:2 | 34% |

The MCT oil mixture "MCT (C8/C10 MIX)" as used herein comprises (i) MCT-C8, (ii) MCT-C10, (iii) MCT(mix C8/C10 2:1) and (iv) MCT(mix C8/C10 1:2). The terms "MCT C8/C10 MIX)" and "MCT(C8/C10 MIX 60:40)" and "MIX" may be interchangeable.

The biodisposition and metabolism of the 8 molecular species in the MCT-mix (C8/C10 MIX 60:40) vary. Hence the overall properties of the MCT(C8/C10 MIX) are the observed average of the 8 species. Moreover, the amount of these 8 species cannot be controlled during the synthetic step and are not fully characterized (see above Table 2).

Rats were orally fed a mixture of MCT-C8 plus MCT-C10 (herein referred to as PLUS) at a 60:40 ratio or a MCT(C8/C10 MIX) oil (herein referred to as MIX). Oral administrations of compound preparations were performed on unanaesthetized freely moving animals using an oral gavage probe. MCT-C8 oil and MIX oil were administered at room-temperature. MCT-C10 oil and PLUS oil were heated until solutions were obtained (at approximately 50° C.) and were administered at approximately 30° C. to the animals.

Blood samples were collected through the catheters implanted on the previous day. For each time point, a sufficient volume of blood was collected and transferred in K3-EDTA tubes in order to get at least 140 microliters of plasma after centrifugation. After each blood sampling, the same volume of saline was administrated to the animal through the catheter both with a small volume of saline containing heparin.

After centrifugation (10 min at 3500 rpm and at 4° C.) and for each blood sample, the volume of plasma collected was split into two aliquots of roughly equal volume (70 µl) and stored at around −60° C. until LC-MS analysis of free fatty acids and ketones (see above).

Results and Discussion

The present inventor found that at the same C8/C10 ratio, a blend of MCT-C8 plus MCT-C10 (PLUS) is superior to MCT(mixC8/10) in providing more plasma C10 free fatty acids when administered to mammals. At the same time, the level of ketone increases by 8%.

Various distinct biological activities have been linked to each C8 fatty acid, C10 fatty acid and ketone species. Hence the ability to modulate the exposure of a subject or tissue of a subject to C8 free fatty acids, C10 free fatty acids and ketones enables the modulation of their overall biological activities.

Figure 2:
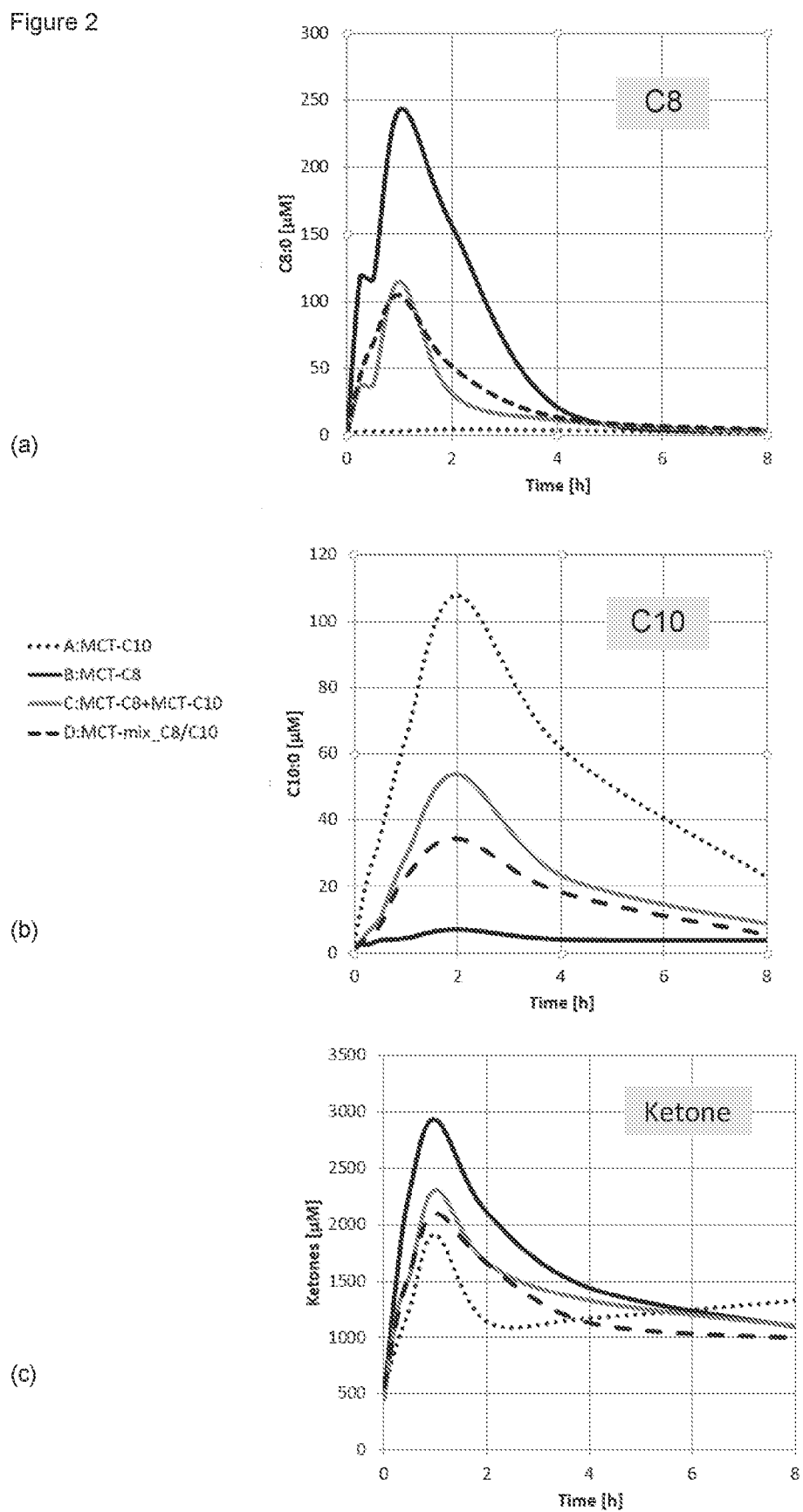
FIG. 2—rats orally fed a mixture of (i) MCT-C8, (ii) MCT-C10, (iii) MCT-C8 plus MCT-C10 (PLUS) or (iv) MCT(C8/C10MIX) oil (MIX). The level of C8 free fatty acids, C10 free fatty acids and ketones in the plasma of rats is shown in Figures (a), (b) and (c) respectively.
Figure 3:
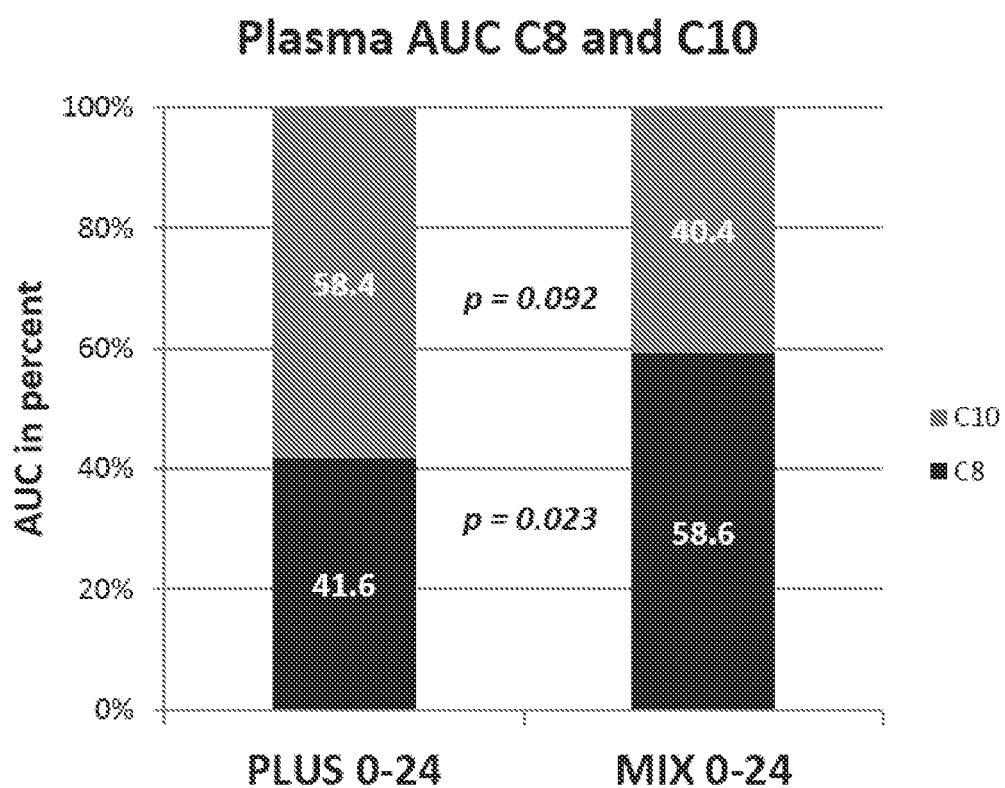
FIG. 3—the AUC of C8 free fatty acid and C10 free fatty acid in plasma over 0 to 24 hours after administration of (i) MCT-C8 plus MCT-C10 (PLUS) or (ii) MCT(C8/C10mix) oil (MIX).

Surprisingly, the present inventor found that in orally fed rats a mixture of MCT-C8 plus MCT-C10 (herein referred to as PLUS) at a 60:40 ratio provides larger plasma C10 free fatty acids than a MCT(C8/C10 MIX) oil (MIX) with the same C8/C10 60:40 ratio. The total MCFA AUC (C8 FFA and C10 FFA) remains the same in PLUS and in MIX. See FIG. 2.

At the same time, the ketone level of PLUS as determined by AUC over the first 8 hours is greater by about 8% compared to the ketone produced by MIX (Table 3).

TABLE 3 plasma ketone exposure over 8 hours

|  | AUC (microM/h) |
|---|---|
| Plus | 11365 |
| Mix | 10484 |

TABLE 4

Plasma C8 FFA and C10 FFA exposure over 24 hours

|  | AUC (microM/h) | | AUC % | |
|---|---|---|---|---|
|  | C8 | C10 | C8 | C10 |
| PLUS 0-24 | 216 | 304 | 41.6 | 58.4 |
| MIX 0-24 | 315 | 214 | 58.6 | 40.4 |
| p | 0.023 | 0.092 |  |  |

All publications mentioned in the above specification are herein incorporated by reference. Various modifications and variations of the described compositions or uses of the present invention will be apparent to those skilled in the art without departing from the scope and spirit of the present invention. Although the present invention has been described in connection with specific preferred embodiments, it should be understood that the invention as claimed should not be unduly limited to such specific embodiments. Indeed, various modifications of the described modes for carrying out the invention, which are obvious to those skilled in biochemistry and biotechnology or related fields, are intended to be within the scope of the following claims.

The invention claimed is:

1. A method of treating an individual having a brain energy deficiency condition or disease, the method comprising administering a composition comprising medium-chain triglycerides (MCTs) to the individual, wherein the MCTs comprise:
   a MCT comprising three fatty acid moieties each with 8 carbon atoms (MCT-C8); and
   a MCT comprising three fatty acid moieties each with 10 carbon atoms (MCT-C10);
   wherein the ratio of the MCT-C8 to the MCT-C10 is from 10:90 to 90:10 (mol/mol), and
   wherein the combined amount of MCT-C8 and MCT-C10 is at least 50 mol % of the MCTs in the composition, and
   wherein the composition provides increased ketones and/or fatty acids as compared to a composition comprising MCTs comprising three fatty acids moieties each with a mix of C8 and C10 moieties attached and having the same C8/C10 ratio and molar amounts.

2. The method according to claim 1 wherein the ratio of MCT-C8 to MCT-C10 is 20:80 to 85:15 (mol/mol).

3. The method according to claim 1 wherein the combined amount of MCT-C8 and MCT-C10 is at least 90 mol % of the MCTs in the composition.

4. A method of treating an individual having a brain energy deficiency condition or disease, the method comprising administering a composition comprising medium-chain triglycerides (MCTs) to the individual, wherein the MCTs comprise:
   a MCT comprising three fatty acid moieties each with 8 carbon atoms (MCT-C8); and
   a MCT comprising three fatty acid moieties each with 10 carbon atoms (MCT-C10); and
   wherein the ratio of the MCT-C8 to the MCT-C10 is from 50:50 to 67:33 (mol/mol), and
   wherein the composition provides increased ketones and/or fatty acids as compared to a composition comprising MCTs comprising three fatty acids moieties each with a mix of C8 and C10 moieties attached and having the same C8/C10 ratio and molar amounts.

5. The method according to claim 1, wherein the three fatty acid moieties each with 8 carbon atoms are octanoic acid moieties, and/or the three fatty acid moieties each with 10 carbon atoms are decanoic acid moieties.

6. The method according to claim 1, wherein the composition further comprises one or more agents that promote or sustain neurologic health or enhance cognitive function, wherein the one or more agents are selected from the group consisting of vitamins, choline, phosphatidylserine, alpha-lipoic acid, CoQ10, acetyl-L-carnitine, herbal extracts, omega-3 or omega-6 polyunsaturated fatty acids, aliphatic ester, fish oil extracts, and mixtures thereof.

7. The method according to claim 4, wherein the three fatty acid moieties each with 8 carbon atoms are octanoic acid moieties, and/or the three fatty acid moieties each with 10 carbon atoms are decanoic acid moieties.

8. The method according to claim 4, wherein the composition further comprises one or more agents that promote or sustain neurologic health or enhance cognitive function, wherein the one or more agents are selected from the group consisting of vitamins, choline, phosphatidylserine, alpha-lipoic acid, CoQ10, acetyl-L-carnitine, herbal extracts, omega-3 or omega-6 polyunsaturated fatty acids, aliphatic ester, fish oil extracts, and mixtures thereof.

9. The method according to claim 1, wherein the ratio of the MCT-C8 to the MCT-C10 is 58:42 to 62:38 (mol/mol).

10. The method according to claim 1, wherein the condition or disease is selected from the group consisting of a brain energy deficiency, a neurological condition, migraine, memory disorder, age-related memory disorder, brain injury, stroke, amyloid lateral sclerosis, multiple sclerosis, cognitive impairment, cognitive impairment post-intensive care, age-induced cognition impairment, Alzheimer's disease, Parkinson's disease, Huntingdon's disease, an inherited metabolic disorder, bipolar disorder, schizophrenia, epilepsy and combinations thereof.

11. The method according to claim 4, wherein the condition or disease is selected from the group consisting of a brain energy deficiency, a neurological condition, migraine, memory disorder, age-related memory disorder, brain injury, stroke, amyloid lateral sclerosis, multiple sclerosis, cognitive impairment, cognitive impairment post-intensive care, age-induced cognition impairment, Alzheimer's disease, Parkinson's disease, Huntingdon's disease, an inherited metabolic disorder, bipolar disorder, schizophrenia, epilepsy and combinations thereof.

12. The method according to claim 10, wherein the inherited metabolic disorder is selected from the group consisting of glucose transporter type 1 deficiency syndrome, pyruvate dehydrogenase complex deficiency, and combinations thereof.

13. The method according to claim 11, wherein the inherited metabolic disorder is selected from the group consisting of glucose transporter type 1 deficiency syndrome, pyruvate dehydrogenase complex deficiency, and combinations thereof.

* * * * *